US005789745A

United States Patent [19]
Martin et al.

[11] Patent Number: 5,789,745
[45] Date of Patent: Aug. 4, 1998

[54] ION MOBILITY SPECTROMETER USING FREQUENCY-DOMAIN SEPARATION

[75] Inventors: Stephen J. Martin; Michael A. Butler, both of Albuquerque; Gregory C. Frye, Cedar Crest; W. Kent Schubert, Albuquerque, all of N. Mex.

[73] Assignee: Sandia Corporation, Albuquerque, N. Mex.

[21] Appl. No.: 959,659

[22] Filed: Oct. 28, 1997

[51] Int. Cl.$^6$ ...................................... H01J 49/40
[52] U.S. Cl. .................. 250/286; 250/287; 250/281; 250/282
[58] Field of Search .................. 250/286, 287, 250/281, 282

[56] References Cited

U.S. PATENT DOCUMENTS

| | | |
|---|---|---|
| 4,633,083 | 12/1986 | Knorr et al. |
| 4,707,602 | 11/1987 | Knorr. |
| 4,855,595 | 8/1989 | Blanchard ........................ 250/286 |
| 4,926,056 | 5/1990 | Spindt. |
| 5,401,963 | 3/1995 | Sittler. |
| 5,541,408 | 7/1996 | Sittler. |

OTHER PUBLICATIONS

Bennett, W.H., "Radiofrequency Mass Spectrometer," *J. Applied Physics,* vol. 21, pp. 143–149 (1950).
Blanchard, W.C., "Using Nonlinear Fields in High Pressure Spectrometry," *Int'l J of Mass Spec and Ion Proc.,* vol. 95, pp. 199–210 (1989).
Eiceman, G.A., "Ion Mobility Spectrometry," *CRC Press,* Textbook, pp. 2–18 and 30 and 154–155 and 158–159 and 198–203.
St. Louis, R.H., et al., "Ion Mobility Spectrometry in Analytical Chemistry," *Anal. Chem.,* vol. 21, Issue 5, pp. 321–355 (1990).

*Primary Examiner*—Kiet T. Nguyen
*Attorney, Agent, or Firm*—John P. Hohimer

[57] ABSTRACT

An apparatus and method is provided for separating and analyzing chemical species in an ion mobility spectrometer using a frequency-domain technique wherein the ions generated from the chemical species are selectively transported through an ion flow channel having a moving electrical potential therein. The moving electrical potential allows the ions to be selected according to ion mobility, with certain of the ions being transported to an ion detector and other of the ions being effectively discriminated against. The apparatus and method have applications for sensitive chemical detection and analysis for monitoring of exhaust gases, hazardous waste sites, industrial processes, aerospace systems, nonproliferation, and treaty verification. The apparatus can be formed as a microelectromechanical device (i.e. a micromachine).

35 Claims, 4 Drawing Sheets

ION MOBILITY SPECTROMETER USING FREQUENCY-DOMAIN SEPARATION

GOVERNMENT RIGHTS

This invention was made with Government support under Contract No. DEAC04-94AL85000 awarded by the U.S. Department of Energy. The Government has certain rights in the invention.

BACKGROUND OF THE INVENTION

1. Field of the Invention (Technical Field)

The present invention relates to analytical devices, such as ion mobility spectrometers, that separate ions for analysis on the basis of ion mobility.

2. Background Art

Ion mobility spectrometry (IMS) refers to the characterizing of chemical substances through gas phase ion mobilities; IMS characterization is especially useful for measuring extremely low concentrations of gaseous species. In modern analytical IMS methods, ion mobilities are determined from ion velocities that are measured in a drift tube with supporting electronics. Ion mobilities are characteristic of particular chemical substances, and can provide a means for detecting and identifying chemical vapors.

IMS has been used for many years to separate compounds and to analyze their concentrations. The devices have demonstrated a high sensitivity for the detection of drugs, explosives, and chemical warfare agents at the 0.1 part-per-billion (ppb) level and lower. The technique as practiced in the prior art consists generally of the following basic steps:

1. Ionization: A vapor sample is introduced into the reaction region of a drift tube, typically by way of a carrier gas, where neutral vapor molecules undergo ionization. The vapor molecules can be ionized through a variety of means. The ionization process produces a mixture of reactant ions and product ions. For example, a proton-transfer ionization process reacts M, a neutral vapor molecule, with $H(H_2O)_n^+$ producing $MH^+$ and n molecules of $H_2O$; the resulting ion mixture therefore contains proton reactant ions and $MH^+$ product ions. Different product ions will be produced for each different neutral gas molecule in the original vapor sample to be analyzed. Through a control means, such as a wire grid, the ions are then allowed into a drift region for separation.

2. Separation: The drift region typically consists of a series of surrounding electrodes. Different voltages are applied to each electrode creating an electric field that forces the ions down the drift tube. A drift gas typically flowing countercurrent to the moving ions at a very slow rate compared to the rate of ion motion obstructs ion motion. Typically operating at atmospheric pressure, the ions collide frequently with molecules of the countercurrent drift gas, which causes the ions to separate according to their mobility (i.e. their ability to avoid collisions with the molecules of the drift gas).

Ion mobility is referenced to the drift gas, and is a function of ion mass, shape, size, and charge distribution (see R. H. St. Louis and H. H. Hill, "Ion Mobility Spectrometry in Analytical Chemistry," *Analytical Chemistry*. 21, 321 (1990)). Ions with larger collisional cross sections travel slower through a drift gas, and therefore have lower mobilities. Separation techniques that isolate ions on the basis of time of travel, as the prior art IMS techniques do, are known as "time-of-flight" separation techniques. Ion mobility (K) can be determined from the ion drift velocity ($v_d$) and the electric field (E) of the drift region at atmospheric pressure:

$$K = \frac{v_d}{E}$$

3. Detection: As the reactant and product ions of each chemical species are pushed down the drift region, the ions are collected by a detecting plate electrode or ion detector at the end of the drift tube. The detected ions generate a current in the detecting plate electrode which can be measured and recorded in the form of an ion mobility spectrum. The ion mobility spectrum typically consists of peaks of ion current versus ion drift time. The ions of greatest mobility exit the column in the least amount of time, and therefore produce the earliest peaks in the ion mobility spectrum.

Although IMS has been successfully used to separate and measure trace chemical species for many years, the technique as practiced in the prior art has several shortcomings which are overcome by the present invention. A conventional IMS device has typically required high voltages to generate the necessary electric field to push the ions against the drift gas. The conventional IMS device further requires a relatively long drift channel to adequately separate the ions through the time-of-flight mechanism. Consequently, the prior art IMS devices are relatively large and expensive. While several attempts have been made heretofore to miniaturize the IMS devices, because they rely on a time-of-flight method for separating species, the reduction in size has generally resulted in a corresponding reduction in resolution.

The present invention overcomes the difficulty of miniaturizing the IMS device by replacing the time-of-flight separation mechanism with a frequency-domain separation technique never before applied to IMS. Because the frequency-domain separation technique does not separate the ions based on their time of travel through the drift region, the IMS apparatus of the present invention can be made in miniature form as a microelectromechanical device (i.e. a micromachine) using microelectronic fabrication techniques.

The present invention comprises the application of the frequency-domain separation technique to IMS as well as to the formation of a micromachined ion mobility spectrometer apparatus that is enabled by such technique. Combining micromachining capabilities and the frequency-domain separation technique allows the IMS apparatus of the present invention to be made small and relatively inexpensive, to operate at low voltage, and to be compatible with the fabrication of on-chip electronic circuitry for operation and control of the IMS apparatus.

Frequency-domain separation has been used in the chemical analysis art before, but it has never been applied to IMS. For example, a frequency-domain technique has been applied to mass spectrometry, and was first reported in 1950 (see W. H. Bennett, "Radiofrequency Mass Spectrometer," *Journal of Applied Physics:* 21, 143–149 (1950)). The mass spectrometry frequency-domain separation teachings are not directly applicable to IMS because the two analysis techniques are quite different. Mass spectrometry separates and measures concentrations of ions on the basis of discrete ion charge to ion mass ratios, rather than on the basis of ion mobility. Mass spectrometry can also require the use of magnetic fields in addition to electric fields to separate ions which have been accelerated in a vacuum; whereas IMS simply uses electric fields to separate non-accelerated ions, and can operate at atmospheric pressure.

It should also be noted that in one instance, a prior-art IMS device has used nonlinear electric fields (see W. C. Blanchard, "Using Nonlinear Fields in High Pressure Spectrometry," *International Journal of Mass Spectrometry and Ion Processes:* 95, 199–210 (1989)). This device used a periodically reversed nonlinear electric field to siphon ions of undesired mobility out of the drift region, and a nonlinear potential well to trap all remaining ions at a certain electrode position to normalize their drift distances, or, in other words, to negate the past history of the ion motion due to the frequently reversed electric fields. While this technique used a nonlinear electric field, it is notably distinct from the frequency-domain technique of the present invention in that the potential well produced by the nonlinear electric field was stationary (i.e. non-moving) over time. This stationary potential well was used to normalize ion drift distances and not to separate the ions due to any movement of the potential well over time. Thus, all prior art separation techniques are, without exception, dependant upon time-of-flight separation, which prevents the miniaturization of the IMS device.

The present invention uses nonlinear electric fields to create a moving potential well, otherwise termed a traveling potential wave, which pushes ions with mobilities greater than a certain threshold to the detector plate. By varying the velocity of the potential well or by keeping the velocity of the potential constant and varying the electric field strength over time (i.e. between scans), a distribution of ion mobilities can be obtained at very high resolution over a small distance. The present invention surmounts obstacles to miniaturization, thereby allowing the fabrication of a micromachined IMS apparatus.

Another object of the present invention, facilitated by the incorporation of the frequency-domain technique, is to miniaturize the IMS device in the form of a micromachine. The application of micromachining technology to IMS provides several key advantages: (1) photolithographic microelectronic manufacturing techniques produce small, precisely-defined features for defining elements of the IMS apparatus including a plurality of spaced electrodes; (2) microelectronics to operate the instrument can be integrated on-chip with the IMS apparatus; and (3) low unit costs can be attained with batch-processing wherein many IMS instruments are simultaneously fabricated on one or more substrates.

Micro-gas-analyzer systems have been called the "holy grail" of sensors, providing laboratory analytical capabilities in a package the size of a conventional sensor. The micromachined ion mobility spectrometer of the present invention approaches this goal, providing the discriminating power of a spectral measurement in an on-chip system.

The conventional, suitcase-sized ion mobility spectrometer has been used for detecting drugs, explosives, environmental pollutants, fuel constituents, and trace contaminants in semiconductor manufacturing. Since ion currents can be measured at the picoampere level, the IMS detection limits are extremely low, on the order of $10^{-14}$ moles/second. Realizing these capabilities in a small and inexpensive unit using the teaching of the present invention will enable many new applications, including monitoring of treaty verification, non-proliferation, weapon state-of-health, exhaust gases, hazardous waste sites, industrial processes, and aerospace systems.

SUMMARY OF THE INVENTION
(DISCLOSURE OF THE INVENTION)

The present invention is of an apparatus and method for separating and analyzing chemical species comprising: ionizing chemical species; separating the ionized chemical species by mobility, wherein the separation comprises synchronously transporting the ionized chemical species in a moving potential well; and detecting the ionized chemical species. In the preferred embodiment, the synchronous transport occurs in a drift or transport region of an ion flow channel, with the transport region including a plurality of spaced electrodes, and with the synchronous transport preferably being effected via cyclical altering of voltages applied to the electrodes, most preferably programmably applied voltages. The spaced electrodes are preferably ring shaped, and most preferably substantially hexagonal ring shaped. Ionization is by radioactive ionization, photoionization, laser ionization, surface ionization, electric-field ionization, or electrified spray ionization. The potential well in a direction along a central (i.e. longitudinal) axis of the transport region in the ion flow channel can be shaped sinusoidally or saw-toothed by control of the voltages applied to the spaced electrodes (other potential well shapes useful for a particular application can be determined by practice of the present invention). The apparatus can be miniaturized and also can include miniaturized operational electronics located either external to or on a common substrate or chip of the apparatus.

In preferred embodiments of the present invention, microelectronic processing techniques (e.g. integrated circuitry or micromachining processes) can be employed to fabricate one or more ion flow channels in which the ionized chemical species can be generated and separated. In particular, anisotropic etching of a monocrystalline semiconductor substrate (e.g. a silicon substrate) can be used to form a square or approximately hexagonal-shaped ion flow channel, with the spaced electrodes being photolithographically defined and subsequently formed by metal deposition or lift-off processes. Alternately, an isotropic etching can be used to form a generally cylindrical ion flow channel in an amorphous substrate material (e.g. a glass substrate). In a preferred method for forming the IMS apparatus, an upper and a lower substrate can be etched, with each substrate containing one-half of each ion flow channel; and then the two substrates can be sandwiched together to superpose the two halves of the ion flow channel thereby forming an assembled and operational ion flow channel.

A primary object of the present invention is to provide an apparatus and method permitting the use of frequency domain separation in IMS and concomitant benefits of miniaturization and programmability for the detection of trace chemical substances.

Other objects, advantages and novel features, and further scope of applicability of the present invention will be set forth in part in the detailed description to follow, taken in conjunction with the accompanying drawings, and in part will become apparent to those skilled in the art upon examination of the following, or can be learned by practice of the invention. The objects and advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The present invention is a method and apparatus for separating and analyzing chemical species based on ion mobility. The invention comprises the elements of ionization of a vapor sample containing one or more chemicals to be analyzed, separation and transport of the ionized vapor molecules, and detection of the transported ionized molecules. The separation and transport element comprises applying the frequency-domain separation technique to ion separation on the basis of ion mobility. The frequency-domain technique is applied by sequentially exciting a plurality of spaced electrodes in a drift or transport region in an ion flow channel of the apparatus such that a nonlinear electric field is created, forming a moving potential well. The potential well is propagated down the transport region at a variable velocity, which selectively and synchronously transports ions of certain mobilities to the detector, thereby effectively discriminating against ions of differing ion mobilities. In some embodiments of the present invention, the velocity of the moving potential well can be fixed, with the strength of the electric field varying over time (i.e. between scans).

The invention further comprises miniaturizing the apparatus of the present invention by using microelectronic processing techniques. These microelectronic processing techniques preferably comprise fabricating one or more ion flow channels, or parts thereof, by etching a substrate, with a plurality of spaced electrodes being subsequently deposited on sidewalls of the etched channels. Microelectronic processing techniques can also be used to form an ion source and an ion detector. In some embodiments of the present invention, microelectronic processing techniques can further be used to form electronic circuitry (also termed electronics) and interconnection wiring on the substrate for operation of the apparatus.

Figure 1:
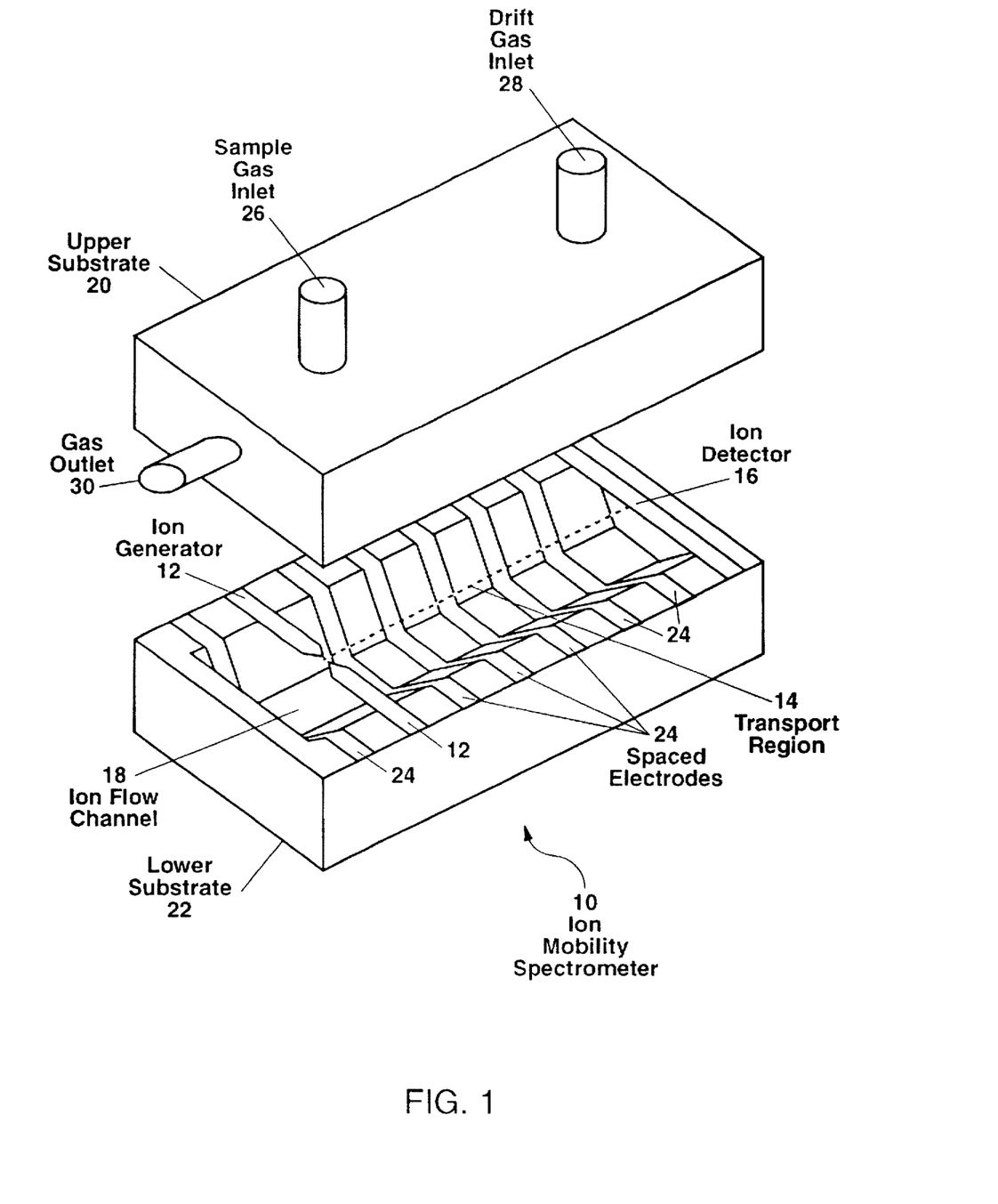
FIG. 1, schematically depicts a preferred embodiment of the micromachined ion mobility spectrometer of the present invention.

FIG. 1 shows a preferred embodiment of the micromachined ion mobility spectrometer (IMS) apparatus 10. Elements of the IMS apparatus 10 include an ion source or generator 12, a transport region 14, and an ion detector 16. Micromachining technology is used in FIG. 1 to fabricate a shaped ion flow channel 18 in which ions can be generated from a sample gas or vapor by interaction with the ion generator 12. The ions are separated for chemical analysis according to ion mobility in the transport region 14 which can comprise the majority of the length of the channel 18.

With a monocrystalline semiconductor substrate, for example silicon (Si) or gallium arsenide (GaAs), an anisotropic etch can be used to form the ion flow channel 18 with sloped sidewalls determined according to the crystalline structure (e.g. along crystalline planes). For a silicon substrate, for example, anisotropic etching can be performed, providing an ion flow channel in the completed IMS apparatus 10 that is approximately hexagonal in shape bounded by (111) crystalline planes. Isotropic etching of an amorphous substrate material such as glass would permit the formation of generally cylindrical channels in the completed IMS apparatus 10.

As shown in FIG. 1, the IMS apparatus 10 is preferably formed by etching shaped ion flow channels of similar dimensions in an upper substrate 20 and a lower substrate 22. A plurality of spaced electrodes, 24 are formed over the substrates, 20 and 22, and on the sidewalls of the ion flow channel 18 by photolithographic definition and metal deposition or lift-off processes. The upper and lower substrates, 20 and 22, can then be sandwiched together to form the completed IMS apparatus 10 with a closed ion flow channel 18. A sample gas inlet 26 can be provided at one end of the ion flow channel 18, preferably near the ion generator 12, and a drift gas inlet 28 can be provided at the other end of the channel 18. A gas outlet 30 can also be provided as shown in FIG. 1 for the sample and drift gases.

There are three primary steps in the IMS apparatus and method of the present invention: ionization of the vapor sample, separation of the ions in the transport region, and detection of the ions.

Ionization

Any method of ionization can be used with the present invention, including radioactive ionization, photoionization (i.e. with photons having an energy greater than an ionization potential of the chemical species to be ionized), laser ionization, surface ionization, electric field ionization, and electrified spray ionization. The preferred method of ionization for use in the device of the invention is electrified spray ionization produced by a corona discharge. Silicon structures made using micromachining are effective corona discharge sources such as described in U.S. Pat. No. 4,926,056, to Spindt.

In FIG. 1, the ion source or generator 12 is formed as a micromachined structure comprising a pair of closely spaced pointed electrodes formed from a semiconductor (e.g. silicon), a metal or a metal alloy. The ion generator 12 operates by applying a bias voltage across the pointed electrodes, thereby ionizing a sample gas provided to the region between the electrodes where a large electric field is present. A flow of a carrier gas can be used to introduce the sample gas into the IMS apparatus 10. Electrodes 24 on either side of the ion generator 12 can be used to apply electric fields that direct the generated ions into the transport region 14 for separation and analysis.

An advantage over the prior art, which collects ions behind a grid until a gating pulse is applied to the grid to allow the ions to enter a time-of-flight channel region, is that, in the present invention, the generated ions are collected in a potential well produced by applying predetermined voltages to the spaced electrodes 24, without the need for a grid. This permits the collection of ions over predetermined and varied periods of time to, if needed, provide for advanced sensitivity for analysis of the chemical sample in an IMS apparatus 10 having a small channel length that can be on the order of one centimeter. With a grid as used in conventional ion mobility spectrometers, both positive and negative ions are collected together, and these oppositely charged ions can recombine over time, thereby limiting the number of ions that can be accumulated for analysis. This deficiency is eliminated in the present invention by the use of a potential well wherein the ions are trapped and transported down the channel 18. In addition, the IMS apparatus 10 of the present invention can separate positive and negative ions at different locations in space since the positive ions are trapped and moved with the potential wells while the negative ions are trapped and moved with peaks in the electrical potential.

Separation

Figure 2A:
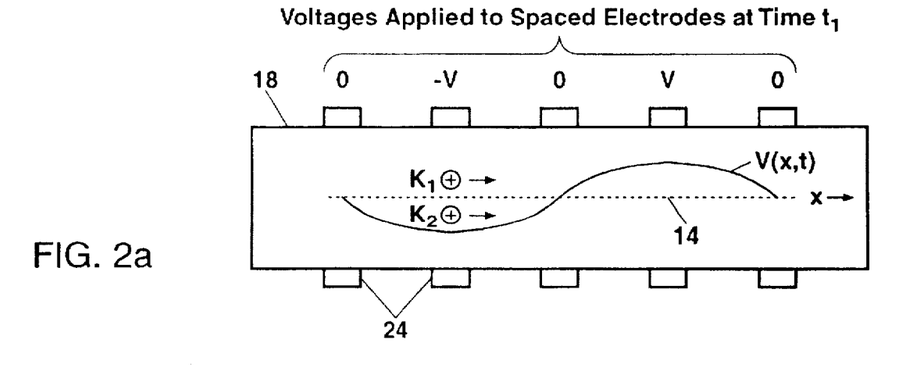
FIGS. 2a–2c schematically depict the frequency-domain separation of ions of different mobilities, $K_1$ and $K_2$, by the use of applied alternating-current voltages to the spaced electrodes to produce a time-varying sinusoidal potential well that synchronously transports ions of mobility $K_1$ while suppressing or retarding the transport of ions of mobility $K_2$.
Figure 2B:
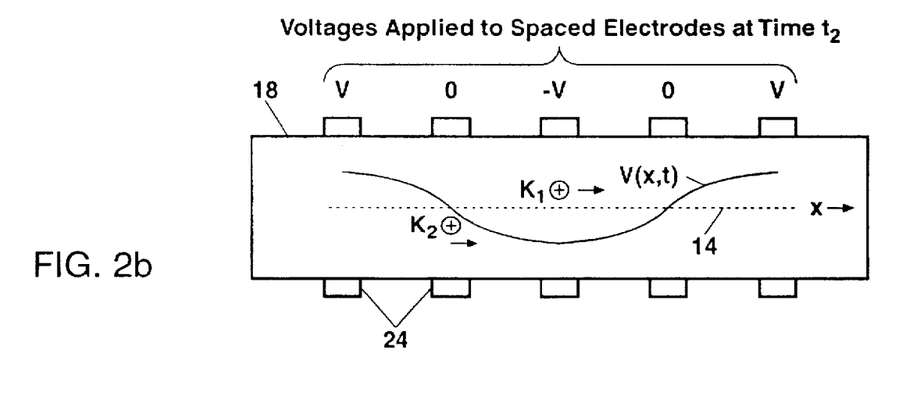
Figure 2C:
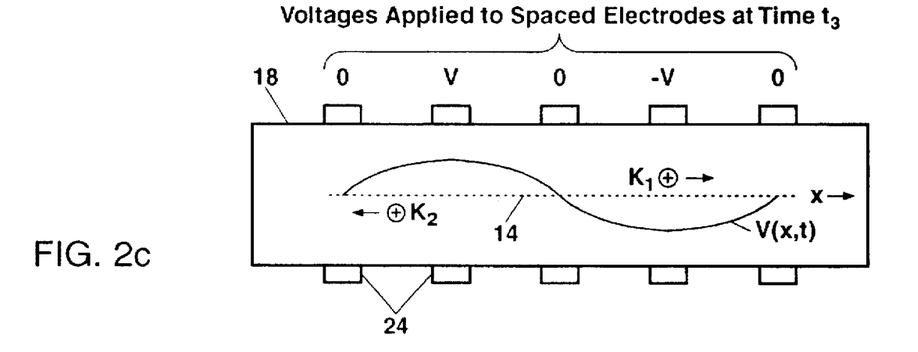

The transport region 14 of the IMS apparatus 10 is surrounded by ring-shaped transport electrodes 24 deposited on sidewalls of the ion flow channel 18, which, in the example of FIG. 1, is substantially hexagonal in shape. Variable programming voltages are applied to each electrode 24 to produce a spatially and temporally varying electric field that is non-linear in the flow direction (i.e. along an x axis as shown in FIGS. 2a–2c), thereby forming a potential well which is moving over time. The voltage potential configuration produced by the electric fields of the electrodes 24 can be of almost any shape that produces a potential well (i.e. a local minimum of electrical potential) to trap ions. In FIGS. 2a–2c, the potential well is shown moving in the x-direction (i.e. towards the ion detector) with the ions of mobility, $K_1$, being transported by the moving potential well while other ions of mobility, $K_2$, remain close to their place of generation, or are oppositely directed.

Figure 3:
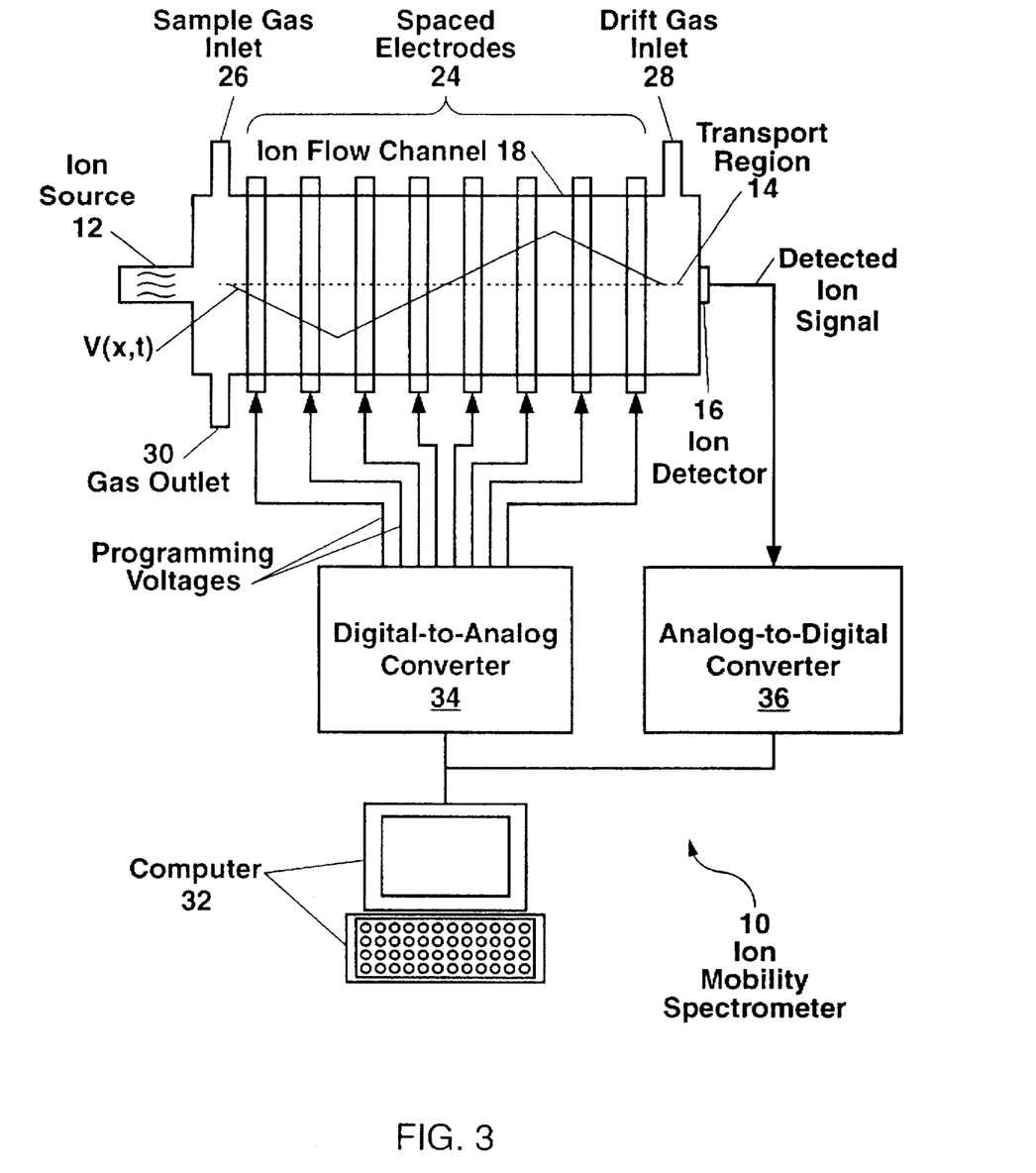
FIG. 3 schematically depicts a frequency-domain separation by a saw-toothed potential wave showing synchronous transport of ions by alternating-current excitation of a plurality of spaced transport electrodes.

In FIG. 2, a smoothly varying sinusoidal potential configuration is shown along the central axis of the transport region 14; whereas in FIG. 3, the potential configuration has a saw-tooth shape. The programming voltages applied to the electrodes 24 are time-varying so that the potential well is made to travel down the flow channel 18 towards the ion detector 16, producing a wave effect, whereby the ions are synchronously urged down the channel 18 when the ion mobility exceeds some threshold level. Ions having a mobility below the threshold level do not reach the ion detector 16 and can be forced in an opposite direction (see FIG. 2c). The frequency-domain technique of the present invention can thus be used to separate ions of a predetermined mobility by controlling the movement of the potential well over time; and ions of different mobilities can be detected if the velocity (defined herein as the rate of change of the position of the potential well with time) of the potential well is scanned or stepped.

FIG. 2a depicts a sinusoidally varying electric potential, V(x,t), in which sinusoidal programming voltages, each of magnitude $V_0$, are applied to the spaced electrodes 24, but with a phase difference between the programming voltages applied to adjacent electrodes 24 of $\Delta\Phi$. The total phase shift along the entire length of the ion flow channel 18 (with $n_{max}$ electrodes) is $\Phi = \eta_{max} \Delta\Phi$. At each electrode, the applied programming voltage $V_n$ is of the form:

$$V_n = V_0 \sin(\omega t + n\Delta\Phi),$$

where n is the electrode number (starting at the beginning of the transport region 14 near the ion source 12), and $\omega$ is an electrode excitation frequency.

At an instant in time, $t_1$, the potential, V(x,t), and thus the electric field, E(x,t), varies sinusoidally down the flow channel 18 as shown in FIG. 2a. FIGS. 2b and 2c show the potential, V(x,t), at different instants of time $t_2 > t_1$ and $t_3 > t_2$ to illustrate movement of the potential well which sweeps ions of mobility $K_1$ towards the ion detector 16 while at the same time effectively discriminating against ions of a different mobility $K_2$ which are prevented from reaching the ion detector 16.

Since adjacent electrodes 24 in FIGS. 2a–2c are excited with a phase lag $\Delta\Phi$ therebetween, a potential minimum (i.e. an energy well) travels down the tube in the x direction at a velocity $V_f$ that is related to the frequency, $\omega$, of the applied programming voltages. When ions are generated by the source 12 and enter the flow channel 18, the ions cluster in one of the potential wells. And if their ion mobilities are sufficiently large, the ions are synchronously transported down the flow channel 18 with the wave propagation (i.e. the moving potential well). A critical mobility, $K_c$, below which the ions will not be carried down the flow channel 18 (i.e., rejected) is determined by the maximum electric field, $E_{max}$, in the wave:

$$K_c = \frac{V_f}{E_{max}} = \frac{L\omega}{\phi E_{max}},$$

where L is the length of the transport region 14. All ions with mobilities larger than $K_c$ are synchronously transported to the ion detector 16. Ions with lesser mobilities are not synchronously transported down the flow channel 18, and therefore are not detected.

The total charge (per potential well minimum) that can be detected is thus given by:

$$Q = \int_{K_c}^{\infty} N(k) dk,$$

where N(k) is the number of ions at a given mobility K. If the charge Q is measured as a function of excitation frequency $\omega$ and differentiated with respect to frequency, N(k) is:

$$N(k) = \frac{\phi E_{max}}{L} \frac{\partial Q}{\partial \omega}.$$

Thus, by varying the applied frequency, $\omega$, the potential well can be moved at different velocities so that ions can be separated according to their ion mobilities to provide for chemical analysis of a gas sample. In other embodiments of the present invention, the frequency, $\omega$, can be kept constant and the maximum electric field, $E_{max}$, in the wave can be varied over time (i.e. between scans) to change $K_c$ (see the above equation for $K_c$ which shows dependences on both $\omega$ and $E_{max}$).

Because the frequency-domain separation technique does not depend on ion drift time, the required length of the transport region 14 can be much shorter than in conventional ion mobility spectrometers. The shorter distance of the transport region 14 translates into a smaller surface area for the surrounding electrodes 24. If the electrodes 24 are closely spaced, a large transport electric field can be achieved with low programming voltages. Electric fields in the 100 Volts/cm range are typical for the conventional IMS, but require applied voltages of several hundred Volts. Electric fields in the 100 Volts/cm range can be achieved with the IMS apparatus 10 of the present invention with much lower programming voltages that are on the order of volts or less, and thus are compatible with integrated circuitry (e.g. CMOS or bipolar circuitry). For example, with electrodes 24 spaced 10 µm apart, only 0.1V potential differences between adjacent electrodes 24 are required.

Detection

The method of detection of ion current is simplified in the present invention due to use of the frequency-domain technique. In conventional ion mobility spectrometers, an electrode plate detector is typically preceded at a distance of a few millimeters by a grid in order to capacitively decouple the detector from an approaching ion packet or swarm. The grid, consisting typically of thin, finely spaced parallel wires, has an appropriate voltage applied to it to maintain the drift field near the detector. Without the grid, the detection plates of the prior-art ion mobility spectrometer would coulombicly feel the ion swarm millimeters before its actual arrival, which would broaden the resulting ion peaks and degrade spectral resolution.

The frequency-domain technique of the present invention separates ions based on their mobility in a moving potential well rather than by time-of-flight as do the prior-art IMS separation techniques. Whereas prior-art ion mobility spectrometers produce a spectrum of ion current versus drift time, the spectrometer of the invention produces a spectrum of ion current (due to detected ion charge) versus potential well velocity.

Figure 4:
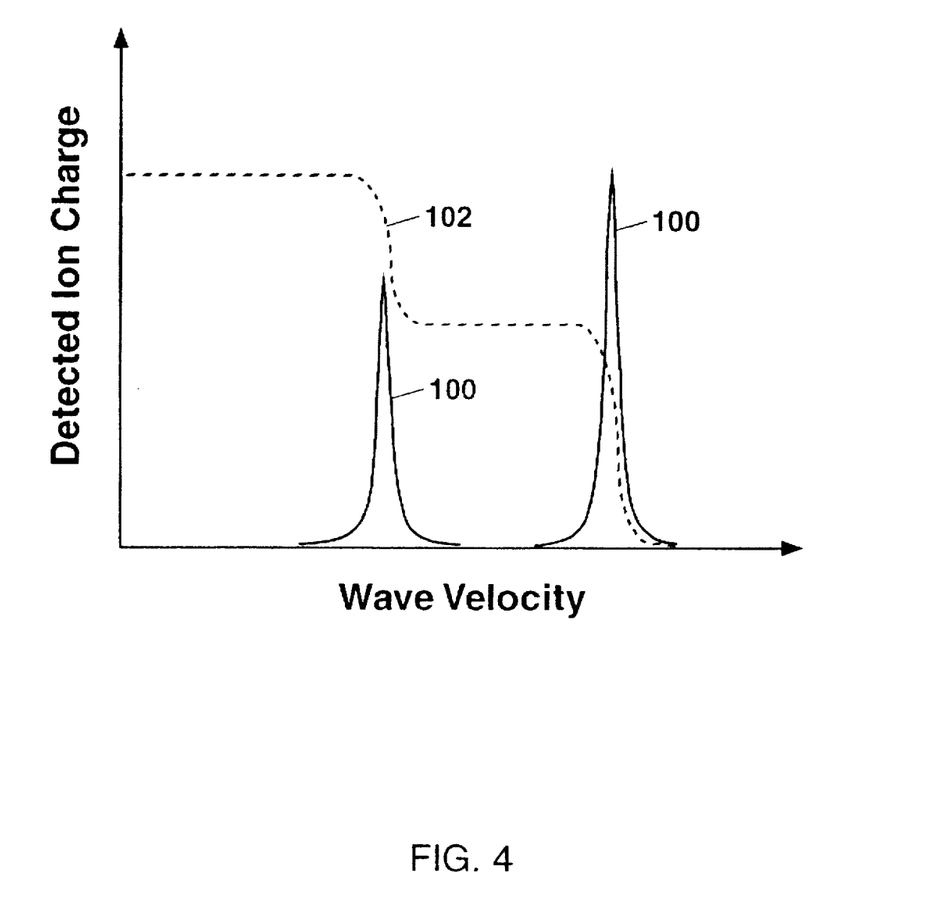
FIG. 4 depicts (as solid curves) packets of two different types of ions trapped and moving with different mobilities in a single potential well of the IMS apparatus, and also depicts (as a dashed curve) the total detected ion charge signal resulting from the detection of these ion packets.

FIG. 4 depicts packets of ions 100 trapped in the moving potential well of the IMS apparatus 10, and the signal resulting from the detection of these ion packets. In FIG. 4, curve 102 represents the detected ion charge (i.e. the ion signal) produced in the ion detector 16 by integration of the charge in each arriving ion packet 100.

When the potential well moves with relatively low velocity through the transport region 14, all ions with a mobility greater than $K_1$ are synchronously transported and detected. But as the well velocity is increased, ions with lower mobilities are periodically left behind the wave (i.e. rejected), and only those ions with mobility greater than $K_2$ are detected. The presence of a particular chemical species can therefore be verified when a particular value of ion mobility corresponding to ions of that chemical species fails to be transported by the potential wave; in other words, the apparatus 10 of the present invention registers the presence of a particular ion species by the ion mobility at which it can no longer be transported down the flow channel 18 to the ion detector 16 by the moving potential well. The mobility, K, of an ion can be calculated from the potential well velocity, $V_f$ at which it is no longer transported by the following relationship:

$$K = \frac{V_f}{E_{max}}$$

Control Hardware and Software

Generation of the appropriate programming voltages on the electrodes 24 as a function of time in the frequency-domain IMS apparatus 10 of the present invention, as well as detection of the ion signal, is a function of the control electronics used. Two approaches can be employed according to the present invention for generation of the programming voltages and thus the traveling potential wave, V(x,t).

An approach that is flexible and of particular use in a laboratory setting is the use of a computer 32 for controlling a digital-to-analog converter 34 having a plurality of outputs connected to the various spaced electrodes 24 as shown in FIG. 3. The detected ion signal can be processed with an analog-to-digital converter 36 and fed back into the computer 32 for analysis and display. With present computers, the programming voltages applied to each electrode 24 can be changed in less than a millisecond. This enables generation of moving potential wells of any predetermined electrical potential shape or configuration via a software program. Accordingly, the potential well velocity and depth (i.e. minimum of electric potential) can be easily adjusted to optimize detection of one or more particular chemical species, or for analyzing a gas sample having an unknown chemical composition.

For certain embodiments of the present invention, an analog approach (or alternately a hybrid analog/digital approach) may be preferred to provide a compact portable IMS apparatus that does not require use of an external computer for control. An example is the use of an analog electronic circuit (e.g. a fixed or variable oscillator circuit) to generate a time varying programming voltage, and a series of phase shifters and/or variable amplifiers connected between the electronic circuit and each electrode 24 to provide the programming voltage to each electrode 24 with a predetermined phase shift, ΔΦ, or amplitude between adjacent electrodes 24 as described heretofore. This analog approach can be implemented in the form of an integrated circuit formed on one of the substrates (e.g. a silicon substrate) used for forming the IMS apparatus.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and applications cited above are hereby incorporated by reference.

What is claimed is:

1. An apparatus for separating and analyzing chemical species, the apparatus comprising:
   a) means for ionizing chemical species;
   b) means for separating the ionized chemical species by mobility, wherein the separating means comprises means for synchronously transporting the ionized chemical species in a moving potential well; and
   c) means for detecting the ionized chemical species.

2. The apparatus of claim 1 wherein the means for synchronously transporting the ionized chemical species in a moving potential well comprises a transport region comprising a plurality of spaced electrodes.

3. The apparatus of claim 2 wherein the means for synchronously transporting the ionized chemical species in a moving potential well further comprises means for cyclically altering voltages on the electrodes.

4. The apparatus of claim 3 wherein the means for cyclically altering voltages on the electrodes is programmable to vary characteristics of the moving potential well.

5. The apparatus of claim 2 wherein the electrodes surround the transport region in a ringed geometry.

6. The apparatus of claim 5 wherein the electrodes surround the transport region in a substantially hexagonal ringed geometry.

7. The apparatus of claim 1 wherein the means for ionizing chemical species comprises means for performing a member selected from the group consisting of: radioactive ionization, photoionization, laser ionization, surface ionization, electric field ionization, and electrified spray ionization.

8. The apparatus of claim 1 wherein the means for synchronously transporting the ionized chemical species in a moving potential well comprises means for propagating the potential well in a sinusoidal electrical potential configuration.

9. The apparatus of claim 1 wherein the means for synchronously transporting the ionized chemical species in a moving potential well comprises means for propagating the potential well in a saw-toothed electrical potential configuration.

10. The apparatus of claim 1 wherein all the means are provided in a miniaturized form on at least one substrate.

11. The apparatus of claim 10 further comprising accompanying miniaturized operational electronics formed on the substrate.

12. The apparatus of claim 10 wherein the miniaturized means comprise an ion flow channel formed in the substrate wherein the ionized chemical species can be generated and separated according to ion mobility.

13. The apparatus of claim 12 wherein the substrate comprises a monocrystalline semiconductor material, and the ion flow channel is anisotropically etched into the substrate.

14. The apparatus of claim 12 wherein the substrate comprises an amorphous material, and the ion flow channel is isotropically etched into the substrate.

15. The apparatus of claim 12 wherein the miniaturized means further includes a plurality of spaced electrodes formed on sidewalls of the ion flow channel.

16. The apparatus of claim 15 wherein the electrodes are photolithographically defined.

17. An apparatus for separating and analyzing chemical species, the apparatus comprising:
   a) a substrate;
   b) an ion flow channel etched into the substrate, and having a transport region wherein a plurality of spaced electrodes are provided for generating a moving electrical potential in response to applied programming voltages;
   c) an ionization source provided at one end of the ion flow channel for ionizing the chemical species and generating ions therefrom; and
   d) an ion detector provided at the other end of the ion flow channel for detecting the ions after traversing the ion flow channel and being separated according to ion mobility.

18. The apparatus of claim 17 wherein the substrate is selected from the group consisting of monocrystalline semiconductor substrates and amorphous substrates.

19. The apparatus of claim 18 wherein the substrate comprises silicon and the ion flow channel is anisotropically etched into the substrate.

20. The apparatus of claim 18 wherein the substrate comprises glass and the ion flow channel is isotropically etched into the substrate.

21. The apparatus of claim 17 wherein the programming voltage change in frequency or amplitude over time.

22. The apparatus of claim 17 wherein the electrical potential has a configuration selected from the group consisting of a sinusoidal configuration and a sawtoothed configuration.

23. The apparatus of claim 17 wherein the electrodes surround the transport region in a ringed geometry.

24. The apparatus of claim 17 wherein the ionization source is selected from the group consisting of a radioactive ionization source, a photoionization source, a laser ionization source, a surface ionization source, an electric field ionization source, and an electrified spray ionization source.

25. A method for separating and analyzing chemical species, the method comprising the steps for:
   a) ionizing chemical species;
   b) separating the ionized chemical species by mobility, wherein the separating step comprises synchronously transporting of the ionized chemical species in a moving potential well; and
   c) detecting the ionized chemical species.

26. The method of claim 25 wherein the step for synchronously transporting the ionized chemical species in a moving potential well is performed in a transport region of an ion flow channel by actuating a plurality of spaced electrodes with programming voltages.

27. The method of claim 26 wherein the transporting step comprises a step for cyclically altering the programming voltages on the electrodes.

28. The method of claim 27 wherein the step for cyclically altering the programming voltages on the electrodes comprises a step for programmably altering the programming voltages to vary characteristics of the moving potential well.

29. The method of claim 26 wherein the electrodes have a ringed geometry.

30. The method of claim 25 wherein the step for ionizing chemical species comprises a step selected from the group consisting of: radioactive ionization, photoionization, laser ionization, surface ionization, electric field ionization, and electrified spray ionization.

31. The method of claim 25 wherein the step for synchronously transporting the ionized chemical species in a moving potential well comprises propagating the potential well in a sinusoidal configuration.

32. The method of claim 25 wherein the step for synchronously transporting the ionized chemical species in a moving potential well comprises propagating the potential well in a saw-toothed potential configuration.

33. The method of claim 25 wherein all steps are performed by miniaturized components formed on a substrate.

34. The method of claim 33 further comprising a step for providing accompanying miniaturized operational electronics on the substrate.

35. The method of claim 33 wherein the step for separating the ionized chemical species by mobility is performed in an ion flow channel, and the ion flow channel is formed by a step for etching the substrate.

* * * * *